US012740710B2

(12) United States Patent
Lee et al.

(10) Patent No.: US 12,740,710 B2
(45) Date of Patent: Sep. 22, 2026

(54) IMAGE FILTERING METHOD

(71) Applicant: MEDIT CORP., Seoul (KR)

(72) Inventors: Dong Hoon Lee, Goyang-si (KR); Seung Jin Lee, Gunpo-si (KR)

(73) Assignee: MEDIT CORP., Seoul (KR)

( * ) Notice: Subject to any disclaimer, the term of this patent is extended or adjusted under 35 U.S.C. 154(b) by 531 days.

(21) Appl. No.: 17/858,993

(22) Filed: Jul. 6, 2022

(65) Prior Publication Data

US 2022/0330831 A1 Oct. 20, 2022

Related U.S. Application Data

(63) Continuation of application No. PCT/KR2021/000223, filed on Jan. 8, 2021.

(30) Foreign Application Priority Data

Jan. 8, 2020 (KR) ........................ 10-2020-0002418

(51) Int. Cl.
*G06T 7/11* (2017.01)
*A61B 5/00* (2006.01)
(Continued)

(52) U.S. Cl.
CPC .............. *A61B 5/0088* (2013.01); *A61B 6/51* (2024.01); *G06T 7/11* (2017.01); *G06T 7/90* (2017.01);
(Continued)

(58) Field of Classification Search
CPC ........... A61B 5/0088; A61B 6/51; G06T 7/11; G06T 7/90; G06T 15/08; G06T 17/00;
(Continued)

(56) References Cited

U.S. PATENT DOCUMENTS 7,698,068 B2 * 4/2010 Babayoff .............. G01J 3/0205 702/19
2014/0177931 A1 * 6/2014 Kocherscheidt ..... A61C 9/0046 382/128

(Continued)

FOREIGN PATENT DOCUMENTS

CN 103679808 A 3/2014
CN 108309493 A 7/2018

(Continued)

OTHER PUBLICATIONS

Extended European Search Report mailed on Nov. 22, 2023 from the European Patent Office for the European Application No. 20738509.5.

(Continued)

*Primary Examiner* — Samir A Ahmed

(57) ABSTRACT

An image filtering method according to the present disclosure comprises: acquiring a two-dimensional image through a scanner, and acquiring color information of at least part of data of the two-dimensional image, and then determining whether the acquired color information is included in a reference color range. When the acquired color information is included in the reference color range, image data remaining after deleting corresponding data from the two-dimensional image is converted into three-dimensional volume data. Meanwhile, when the reference color range is determined, a reference color may be pre-configured data or may be predetermined by a user, or learning for defining a reference color range may be performed through image data acquired by repetitively inputting reference images. By using the image filtering method, a three-dimensional scanner user can minimize post-correction work after scanning and acquire a precise data result value for an interior of the oral cavity, whereby data reliability is enhanced.

12 Claims, 6 Drawing Sheets

(51) Int. Cl.

| | |
|---|---|
| ***A61B 6/51*** | (2024.01) |
| ***G06T 7/90*** | (2017.01) |
| ***G06T 15/08*** | (2011.01) |
| ***G06T 17/00*** | (2006.01) |

(52) U.S. Cl.
CPC .............. *G06T 15/08* (2013.01); *G06T 17/00* (2013.01); *G06T 2207/10081* (2013.01); *G06T 2207/30036* (2013.01)

(58) Field of Classification Search
CPC . G06T 2207/10081; G06T 2207/30036; G06T 2207/10024; G06T 7/579; G06T 5/20; G06T 2207/20024; G06T 2210/41; G06T 5/70
See application file for complete search history.

(56) References Cited

U.S. PATENT DOCUMENTS

| | | | | |
|---|---|---|---|---|
| 2015/0164335 | A1* | 6/2015 | Van Der Poel | A61C 9/0053 433/29 |
| 2015/0209118 | A1* | 7/2015 | Kopelman | A61C 9/0053 433/214 |
| 2018/0028063 | A1* | 2/2018 | Elbaz | A61B 1/24 |
| 2020/0169722 | A1* | 5/2020 | Fisker | G01B 11/2513 |
| 2020/0170760 | A1* | 6/2020 | Dawood | G06T 5/77 |
| 2020/0281700 | A1* | 9/2020 | Kopelman | G06T 7/55 |
| 2020/0352688 | A1* | 11/2020 | Esbech | G01J 3/508 |
| 2021/0106409 | A1* | 4/2021 | Öjelund | G03B 35/02 |
| 2021/0321872 | A1* | 10/2021 | Saphier | A61B 5/7475 |
| 2022/0130045 | A1* | 4/2022 | Kopelman | G16H 30/40 |

FOREIGN PATENT DOCUMENTS

| | | | |
|---|---|---|---|
| CN | 109389669 | A | 2/2019 |
| EP | 1607041 | A2 | 12/2005 |
| JP | 05-143702 | A | 6/1993 |
| JP | 2001-084408 | A | 3/2001 |
| JP | 2007-257087 | A | 10/2007 |
| KR | 10-2015-0057698 | A | 5/2015 |
| KR | 10-2016-0020268 | A | 2/2016 |
| KR | 10-1841441 | B1 | 3/2018 |
| KR | 10-2019-0022941 | A | 3/2019 |
| KR | 10-2019-0103833 | A | 9/2019 |
| WO | 2018/219800 | A1 | 12/2018 |
| WO | 2019/158442 | A1 | 8/2019 |

OTHER PUBLICATIONS

International Search Report mailed May 10, 2021 for PCT/KR2021/000223 and its English translation.

Chinese Office Action mailed on Jun. 23, 2025 from the Chinese Patent Office for Chinese Application No. 202180008625.0.

Chinese Office Action mailed on Sep. 22, 2025 from the Chinese Patent Office for Chinese Application No. 202180008625.0.

* cited by examiner

IMAGE FILTERING METHOD

CROSS-REFERENCE TO RELATED APPLICATIONS

This application is a continuation application of International Application No. PCT/KR2021/000223, filed Jan. 8, 2021, which claims the benefit of Korean Patent Application No. 10-2020-0002418, filed Jan. 8, 2020 in the Korean Intellectual Property Office, the disclosures of which are incorporated herein in their entirety by reference.

TECHNICAL FIELD

The present disclosure relates to an image filtering method, and more specifically, to a method of excluding a part unnecessary for a user from an acquired image.

BACKGROUND ART

A three-dimensional scanning technology is currently being widely used regardless of industrial fields, and its practicality continues to attract attention, particularly in a dental treatment field such as the production of dental prosthetic treatment products.

Meanwhile, when the patient's affected area, that is, the inside of the oral cavity (meaning teeth, gums, or the like) is captured by a three-dimensional scanner, the three-dimensional scanner converts the image of the captured area into three-dimensional volume data to eventually acquire one entire oral cavity model data.

At this time, when the inside of the patient's oral cavity is captured, there is a possibility that foreign substances present in the oral cavity, the hand of a user of the three-dimensional scanner (usually may be a dentist), or the like may be captured together. As described above, the foreign substance or the user's hand is a factor that hinders the acquisition of the patient's entire oral model data, and as a result, needs to be deleted in a three-dimensional volume data conversion process or a post-correction process.

Until now, the user of the three-dimensional scanner manually deletes the part that does not correspond to the inside of the actual oral cavity from the converted three-dimensional volume data after performing the scan, so that there is a problem in that the post-correction operation takes a lot of time.

SUMMARY OF INVENTION

Technical Problem

To solve the above problem, an object of an image filtering method according to the present disclosure is to provide a method of not including pixel data determined as not corresponding to oral cavity information in a three-dimensional volume data conversion process by acquiring color information on each pixel of two-dimensional image data from the acquired two-dimensional image data, comparing the acquired color information with reference color information, and deleting the pixel data determined as not corresponding to the oral cavity information.

In addition, another object of the present disclosure is to provide a method of not including pixel data determined as not corresponding to oral cavity information in a three-dimensional volume data conversion process by defining a reference color a reference color range through learning of the color information to delete the pixel data determined as not corresponding to the oral cavity information from the learned reference color or reference color range.

The objects of the present disclosure are not limited to the above-described technical objects, and other objects not mentioned will be clearly understood to those skilled in the art from the following descriptions.

Solution to Problem

An image filtering method according to the present disclosure may include an image acquiring operation of acquiring a two-dimensional image of a scan target having a valid data part including a tooth inside an oral cavity through a scanner, a color acquiring operation of acquiring color information from at least some data of the two-dimensional image acquired from the image acquiring operation, a filtering operation of determining the at least some data as data to be deleted having a color to be deleted and deleting the data to be deleted within the two-dimensional image data when the color information of the at least some data is included within a reference color range that is a color range of an object to be filtered distinguished from an inside of the oral cavity in the color acquiring operation, and a three-dimensional calculating operation of converting two-dimensional data having only the valid data part by deleting the data to be deleted through the filtering operation into three-dimensional volume data.

In addition, the image filtering method may further include a reference color determining operation of determining whether the color information of the at least some data acquired in the color acquiring operation is included within the reference color range, in which the filtering operation may determine the at least some data determined as the reference color range from the reference color determining operation as the data to be deleted to delete the at least some data within the two-dimensional image data.

In addition, the image filtering method may further include a reference color setting operation of setting the color to be deleted, in which the color to be deleted in the reference color setting operation may be designated through a user interface.

In addition, the size of the reference color range is adjustable through the user interface with respect to the color to be deleted.

In addition, the color information may be information expressed by using an RGB additive color mixture method.

Meanwhile, an image filtering method according to another embodiment of the present disclosure may include an image acquiring operation of acquiring a two-dimensional image of a scan target having a valid data part including a tooth inside an oral cavity through a scanner, a modeling operation of generating a three-dimensional virtual model based on the two-dimensional image, a displaying operation of visually displaying the three-dimensional virtual model, and a filtering operation of filtering a part corresponding to the color to be deleted that is a color of an object to be filtered distinguished from the inside of the oral cavity in the two-dimensional image before the displaying operation, in which wherein the modeling operation may generate the three-dimensional virtual model with the two-dimensional image data having only the valid data part by deleting the data having the color to be deleted.

In addition, the filtering operation may further include a reference color setting operation of setting the color to be deleted from the object to be filtered, and a reference color determining operation of determining whether the color to be deleted exists in the two-dimensional image.

In addition, the reference color setting operation may be set by a user's selection, or set based on the image of the object to be filtered.

Meanwhile, an image filtering method according to still another embodiment of the present disclosure may include an image acquiring operation of acquiring a two-dimensional image of a scan target having a valid data part including a tooth inside an oral cavity through a scanner, a color acquiring operation of acquiring color information from at least some data of the two-dimensional image acquired from the image acquiring operation, a reference color range defining operation of defining a color range of an object to be filtered as a reference color range based on an image of the object to be filtered distinguished from the inside of the oral cavity, a reference color determining operation of determining whether color information of the at least some data acquired in the color acquiring operation is included within the reference color range defined through learning, a filtering operation of determining the at least some data as data to be deleted having a color to be deleted and deleting the at least some data within the two-dimensional image data when the color information of the at least some data is included within the reference color range in the color determining operation, and a three-dimensional calculating operation of converting two-dimensional data having only the valid data part by deleting the data to be deleted through the filtering operation into three-dimensional volume data.

In addition, the reference color range defining operation may include a reference image acquiring operation of repeatedly acquiring at least one image of the object to be filtered including the color to be deleted, and a reference color range learning operation of determining the reference color range from the image of the object to be filtered acquired from the reference image acquiring operation.

In addition, the reference color range learning operation may learn an overlapping color from at least one image acquired through the reference image acquiring operation as the reference color range.

In addition, the color information may be information expressed by using an RGB additive color mixture method.

Advantageous Effects of Invention

According to the present disclosure, it is possible to determine whether the captured part is a part necessary for forming oral cavity model data through a color value of at least a part of an acquired image, and perform a three-dimensional calculation only for a part actually necessary for forming the oral cavity model data by deleting data of the corresponding part when it is determined that the part is a noise pixel having a color to be deleted.

In addition, it is possible to save the time and resource required for the three-dimensional calculation by performing the three-dimensional calculation only for the part necessary for forming the oral cavity model data as described above.

In addition, the three-dimensional volume data is formed with the data excluding the noise pixel, so that it is possible to acquire the more precise three-dimensional volume data, thereby improving the reliability of the oral cavity model data.

DESCRIPTION OF EMBODIMENTS

Figure 1:
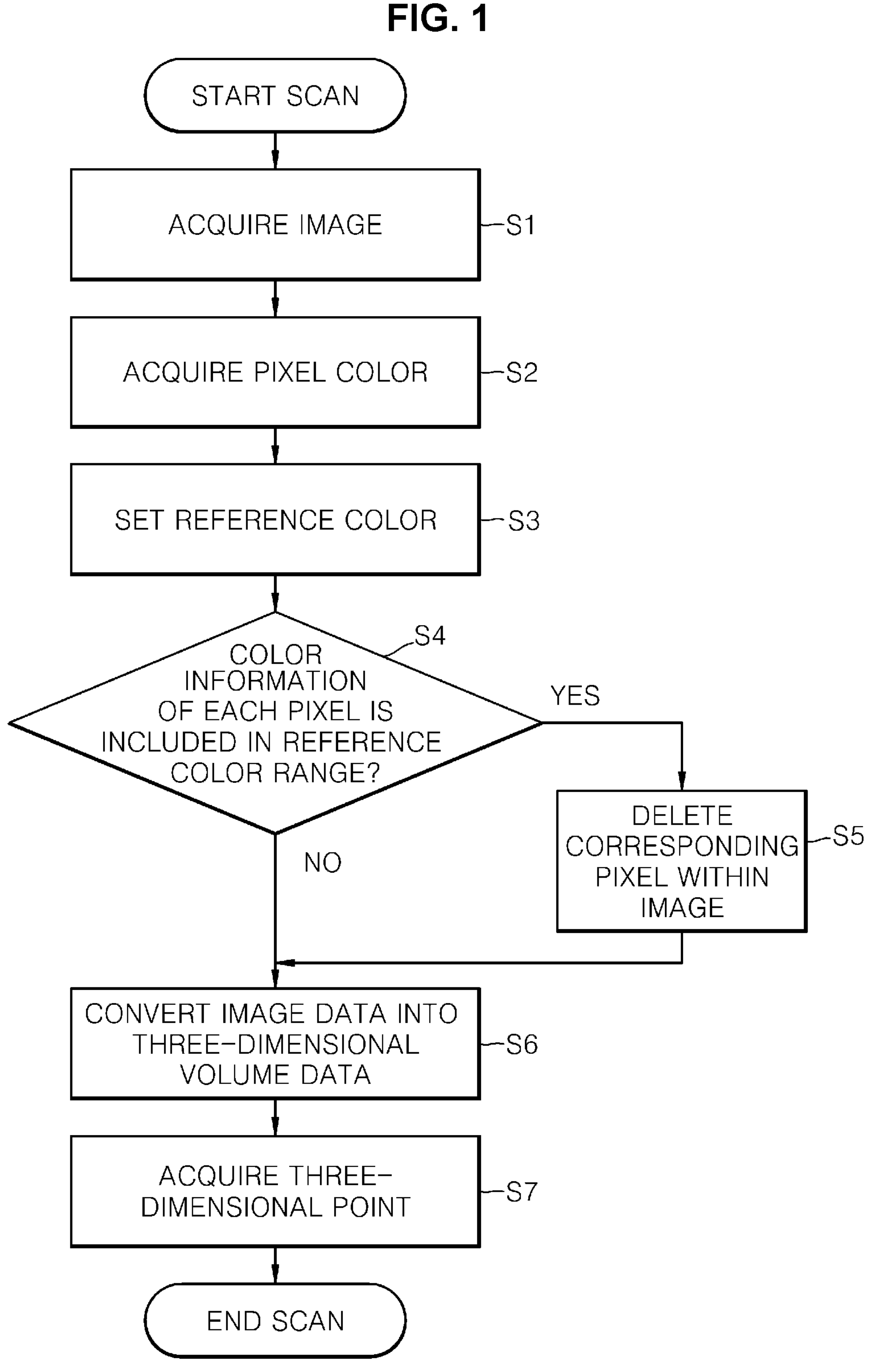
FIG. 1 is a flowchart of an image filtering method according to the present disclosure.

Hereinafter, some embodiments of the present disclosure will be described in detail with reference to exemplary drawings. In adding reference numerals to the components of each drawing, it should be noted that the same components are given the same reference numerals as much as possible even though they are indicated on different drawings. In addition, in describing the embodiment of the present disclosure, when it is determined that a detailed description of a related known configuration or function interferes with the understanding of the embodiment of the present disclosure, the detailed description thereof will be omitted.

In describing the components of the embodiment of the present disclosure, terms such as first, second, A, B, (a), and (b) may be used. These terms are only for distinguishing the component from other components, and the essence, sequence, or order of the component is not limited by the terms. In addition, unless otherwise defined, all terms used herein, including technical or scientific terms, have the same meaning as commonly understood by one of ordinary skill in the art to which the present disclosure pertains. Terms such as those defined in a commonly used dictionary should be interpreted as having a meaning consistent with the meaning in the context of the related art, and should not be interpreted in an ideal or excessively formal meaning unless explicitly defined in the present application.

Figure 2:
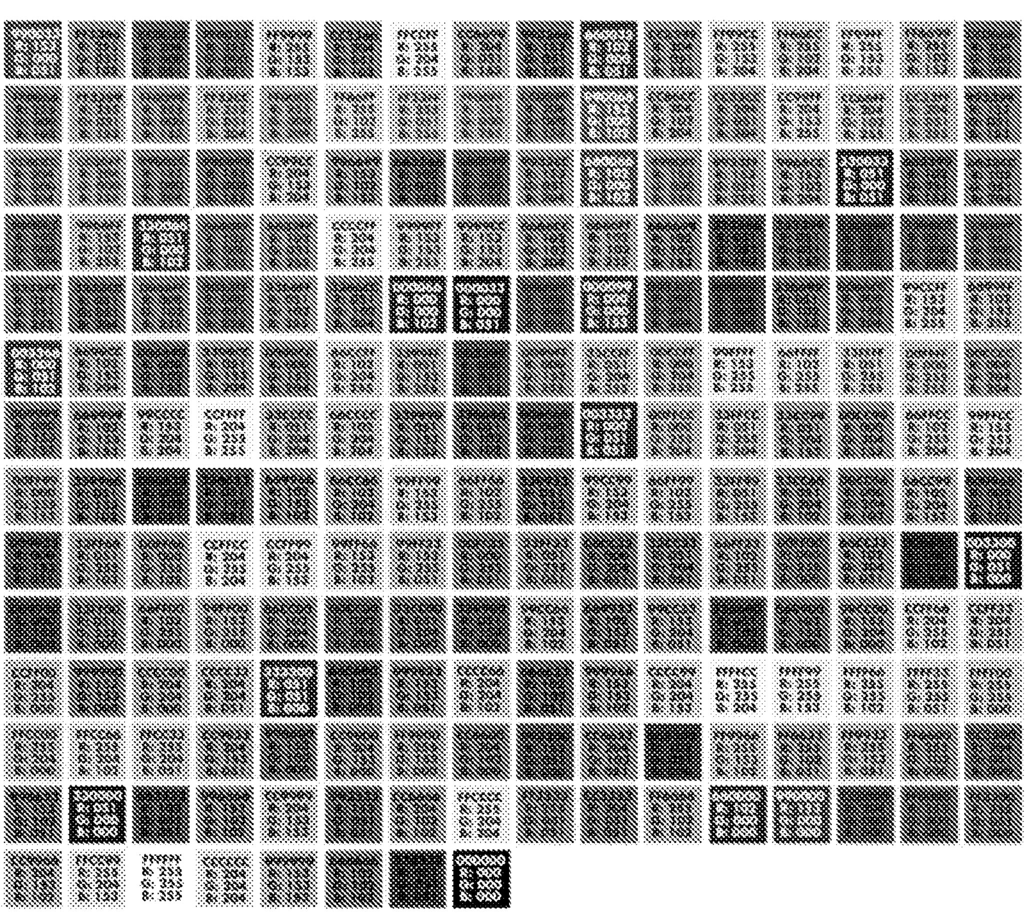
FIG. 2 shows a simplified RGB color table for describing an RGB additive color mixture method in the image filtering method according to the present disclosure.
Figure 3:
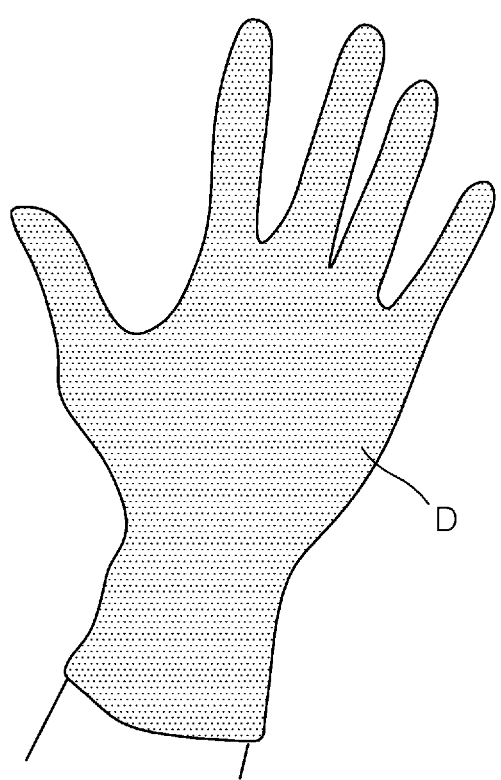
FIG. 3 is a view exemplarily showing an object having a color to be deleted in the image filtering method according to the present disclosure.
Figure 4:
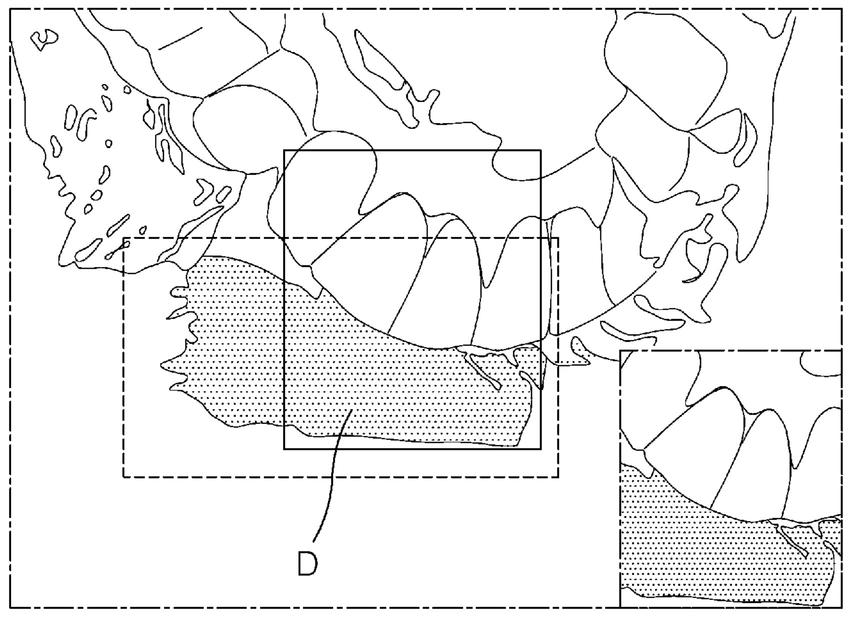
FIG. 4 is a view exemplarily showing that data of the object having the color to be deleted and data inside an oral cavity are converted into three-dimensional volume data together in the image filtering method according to the present disclosure.
Figure 5:
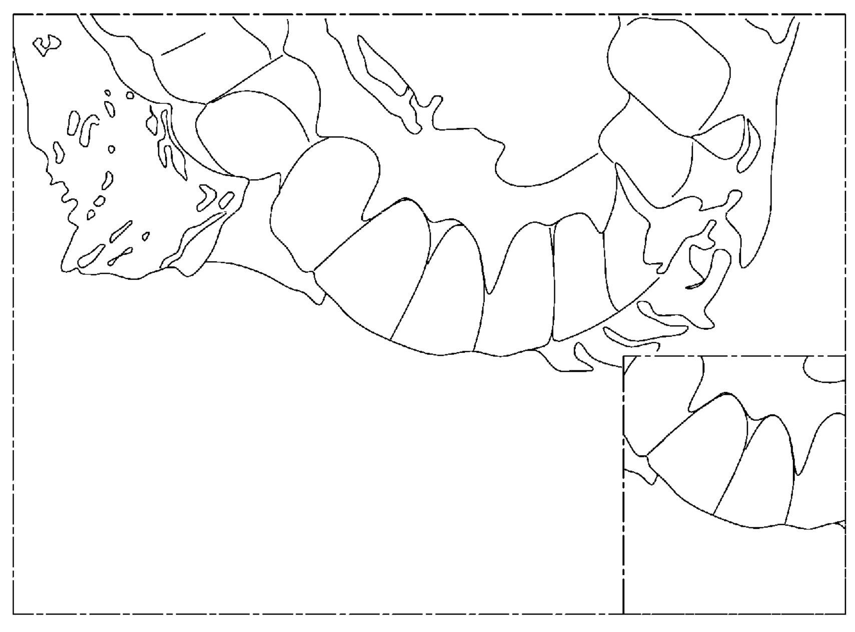
FIG. 5 is a view exemplarily showing that the object having the color to be deleted is excluded and only the data inside the oral cavity is converted into the three-dimensional volume data in the image filtering method according to the present disclosure.

FIG. 1 is a flowchart of an image filtering method according to the present disclosure, and FIG. 2 shows a simplified RGB color table for describing an RGB additive color mixture method in the image filtering method according to the present disclosure. In addition, FIG. 3 is a view exemplarily showing an object having a color to be deleted in the image filtering method according to the present disclosure, FIG. 4 is a view exemplarily showing that data of the object having the color to be deleted and data inside an oral cavity are converted into three-dimensional volume data together in the image filtering method according to the present disclosure, and FIG. 5 is a view exemplarily showing that the object having the color to be deleted is excluded and only the data inside the oral cavity is converted into the three-dimensional volume data in the image filtering method according to the present disclosure.

Referring to FIG. 1, an image filtering method according to the present disclosure may include an image acquiring operation (S1) of acquiring two-dimensional image data through a scanner. When the user of a three-dimensional scanner starts to scan the inside of the patient's oral cavity, the three-dimensional scanner may capture the inside of the patient's oral cavity through an imaging unit formed therein. At this time, the three-dimensional scanner may be formed to have an opening that is drawn into or drawn out from the patient's oral cavity and has an open one side on one end thereof. When light reflected from the affected area (teeth, gums, or the like) to be captured inside the patient's oral cavity is incident into the three-dimensional scanner through the opening, the reflected light is received by at least one camera, which is a component of the imaging unit. The received light is analyzed by an imaging sensor telecommunicatively connected to the camera, and two-dimensional image data is generated as the analysis result of light. The two-dimensional image data refers to data in the form of photos before being converted into three-dimensional volume data.

Meanwhile, a method in which the three-dimensional scanner acquires the image in the above-described image acquiring operation (S1) may be at least one of various measurement methods such as one-dimensional line scan, triangulation through structured light, and confocal. By acquiring the two-dimensional image data according to the above method, information for converting the two-dimensional image data into three-dimensional volume data is collected.

The image acquired in the image acquiring operation is configured in a unit of a pixel. The pixel refers to the smallest unit configuring an image. The two-dimensional image data acquired from the above-described image acquiring operation acquires color information from the number of pixels corresponding to the size of the two-dimensional image data, that is, all pixels of the corresponding two-dimensional image data (S2). At this time, as the acquired color information, an RGB additive color mixture model, an HSV model, a YCbCr model, or the like may be used. Referring to FIG. 2, an RGB model may express color information of a corresponding pixel by combining each of three color elements of red, green, and blue. More specifically, the RGB model may represent the color elements of Red, Green, and Blue as integers from 0 to 255, respectively, in order to express color information of each pixel configuring the two-dimensional image data. Meanwhile, as a color value increases from 0 to 255, the pixel becomes clearer or brighter, and for example, when the RGB value is (0, 0, 0), the pixel may represent black, and when the RGB value is (255, 255, 255), the pixel may represent white.

Meanwhile, referring to FIG. 3, the user only needs data necessary for treating the patient, such as teeth and gums, in the two-dimensional image data (this will be referred to as 'valid data' in this specification). Other data are referred to as data unnecessary for treating the patient, and the unnecessary data is referred to as noise data. The noise data may be data on all objects unnecessary for dental treatment, and for example, include the user's hand (usually, a hand wearing a sanitary glove having a color distinguished from the colors of teeth or gums inside the oral cavity due to the nature of the dental treatment), saliva, or other foreign substances. When the noise data is included in a scan area, the noise data is acquired together with valid data in the form of two-dimensional image data. In other words, a scan target may include not only an object corresponding to the valid data but also an object corresponding to the noise data. Accordingly, converting the noise data into the three-dimensional volume data together with the valid data and then removing the noise data in the post-correction operation consumes an operation amount and operation time unnecessary in the three-dimensional volume data conversion process.

Accordingly, the image filtering method according to the present disclosure may further include a reference color setting operation (S31) of setting a color to be deleted. The reference color setting operation enables the user to set a color desired to be deleted (a color to be deleted or a reference color) on a user interface (UI), that is, a color of a part corresponding to the noise data in the scan target. After the color to be deleted is set, the corresponding part of the pixel including the color to be deleted in the two-dimensional image data may be deleted so as not to be included in the three-dimensional volume data conversion target. Meanwhile, the reference color setting operation may include the color to be deleted that is systematically predetermined in addition to the color to be deleted directly designated by the user, and include that the user changes, adds, or deletes the systemically predetermined color according to the user's needs. For example, in the reference color setting operation S31, the user may directly designate the color to be deleted using a color picker. At this time, the user may also designate the color to be deleted on any acquired two-dimensional image data, or may also designate the color to be deleted on a color palette.

However, an object to be deleted by the user may also be expressed in only one color, but may also be acquired as having a plurality of color information when considering the reflection of the shadow when the object is captured by the three-dimensional scanner. At this time, the size of the reference color range may be adjusted based on the color to be deleted. In other words, when one color of the object to be deleted is designated, up to colors adjacent to the color may be set to the reference color range. Meanwhile, the reference color range may not be equally applied to all scan situations, and the size of this range may be adjusted through the user interface. For example, up to wider adjacent colors are set to the reference color area by setting a wide reference color range, so that the range to be deleted may be increased, and up to narrower adjacent colors are set to the reference color area by setting a narrow reference color range, so that the range to be deleted may be decreased. In addition, when the color to be deleted is designated in the above-described reference color setting operation (S31), colors within a predetermined range from the RGB color values of the color to be deleted may be set to the reference color range. For example, when the RGB value of the specified color to be deleted is (x, y, z), an R (Red) value of the reference color range may have a range from $x-\alpha$ to $x+\alpha$, a G (Green) value may have a range from $y-\beta$, to $y+\beta$, and a B (Blue) value may have a range from $z-\gamma$ to $z+\gamma$ ($\alpha$, $\beta$, and $\gamma$ are arbitrary integers). In other words, by setting the reference color range or adjusting the reference color range in consideration of environmental changes that may occur in the scan process, the user may efficiently remove the noise data, and minimize the post-correction operation.

When the color information acquired from the two-dimensional image and the reference color range are set, whether color information of some acquired data is included in the reference color range may be compared and determined (S4). For example, the parts corresponding to the valid data of the scan will have at least some of all colors that do not basically correspond to the reference color range, but may usually have white or ivory of teeth, and red or pink colors of gums or the like. On the other hand, the noise data may have a color different from the color of the inside of the oral cavity, and the color information of each pixel of the two-dimensional image data acquired by capturing the noise data may be included in the reference color range.

As described above, when it is determined that the part corresponding to the noise data is included in the reference color range, a calculation unit determines the corresponding part as a pixel having the color to be deleted to delete the part in the two-dimensional image data (filtering operation (S5)). In other words, since the data within the reference color range is not data about the inside of the oral cavity to be acquired, the amount of calculation for the conversion into three-dimensional volume data is reduced by deleting the data within the reference color range in advance before performing the conversion into the three-dimensional volume data. As described above, by deleting (filtering) the data included in the reference color range, there is an advantage in that it is possible to shorten an execution time of the subsequent operation.

When the above-described filtering operation (S5) is completed, the calculation unit converts the completely filtered two-dimensional image data into three-dimensional volume data (three-dimensional calculating operation (S6)), and visually displays the three-dimensional volume data (displaying operation). At this time, the part converted into the three-dimensional volume data is a part corresponding to valid data such as teeth and gums among scan targets, and the part corresponding to the noise data is preemptively removed before being displayed and is not visually displayed in the displaying operation. Accordingly, the reliability of the oral cavity model data formed by the three-dimensional volume data is improved. As described above, the calculation amount of data to be converted as a whole is reduced by performing a three-dimensional volume data conversion calculation after the filtering operation (S5), and as a result, there is an advantage in that the calculation speed may be increased and the time required for the calculation may be reduced, thereby acquiring the reliable entire oral cavity model data in a shorter time. Comparing and referring to FIGS. 4 and 5, in FIG. 4, the color to be deleted is converted into the three-dimensional volume data as it is and needs to be deleted through post-correction. On the other hand, in FIG. 5, since the noise data is preemptively removed from the two-dimensional image data, it may be seen that the noise data has been excluded from calculation in the three-dimensional volume data conversion.

Meanwhile, the three-dimensional volume data converted from the two-dimensional image data may have a form in which a plurality of points are connected in a mesh form. Accordingly, three-dimensional points included in the three-dimensional volume data may be acquired (S7). The three-dimensional volume data may be analyzed and transformed by using the three-dimensional points, and more suitable treatment may be provided to the patient by analyzing and modifying the three-dimensional volume data.

Hereinafter, an image filtering method according to another embodiment will be described. In the following description, the above-described content will be briefly mentioned or omitted.

Figure 6:
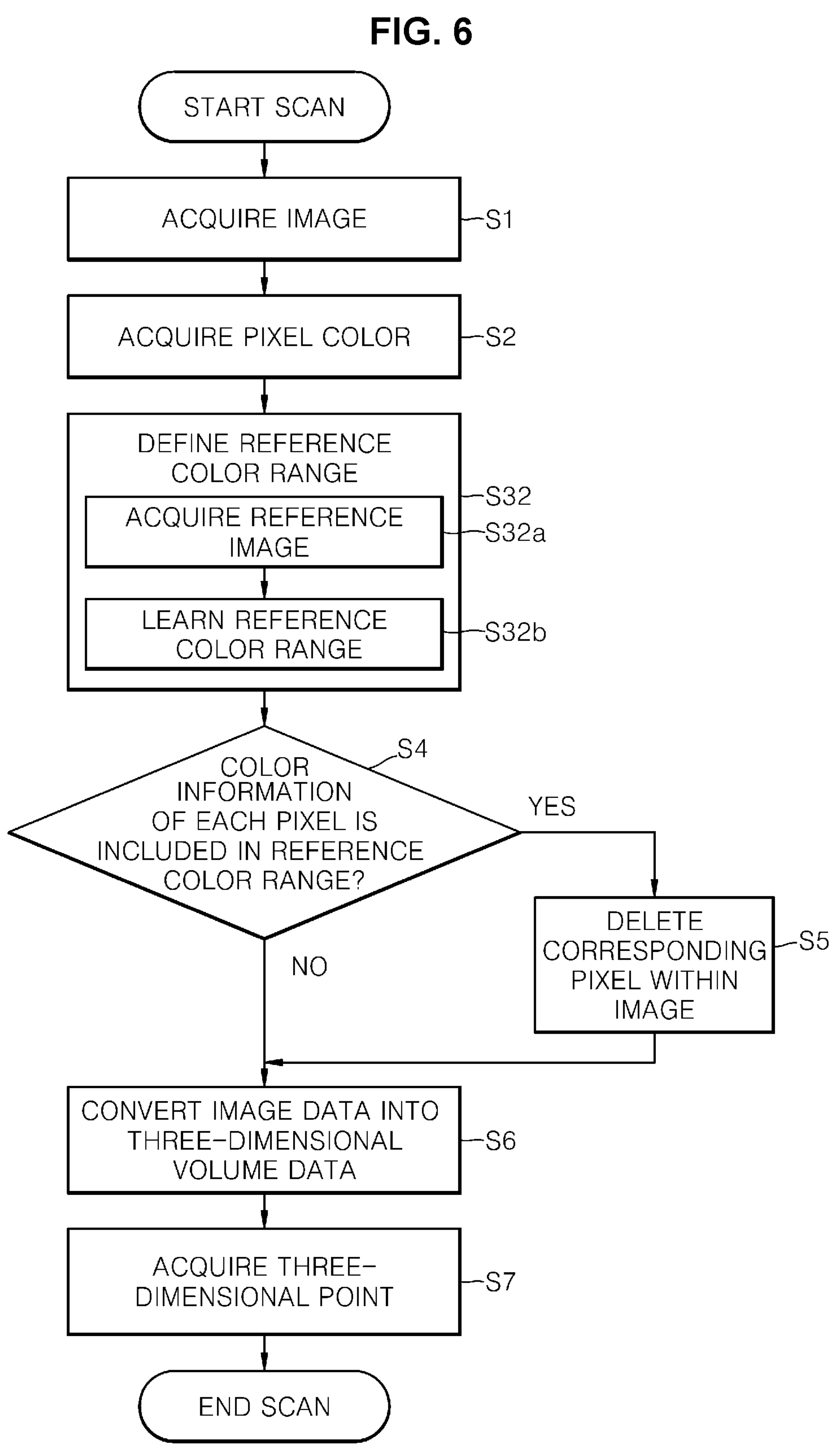
FIG. 6 is a flowchart of an image filtering method according to another embodiment of the present disclosure.

FIG. 6 is a flowchart of an image filtering method according to another embodiment of the present disclosure.

Referring to FIG. 6, the image filtering method according to the present disclosure includes an image acquiring operation (S1) of acquiring two-dimensional image data through a three-dimensional scanner by a user, and a color acquiring operation (S2) of acquiring color information from at least a part of the acquired two-dimensional image data. The image acquiring operation (S1) and the color acquiring operation (S2) are the same as described above, and thus are omitted.

Meanwhile, the image filtering method according to the present disclosure may further include a reference color range defining operation (S32) of defining a reference color range by color information acquired together by acquiring an image of an object to be filtered. Differently from the above-described reference color setting operation (S31), the reference color range defining operation (S32) means that the reference color range is automatically defined from the color information acquired together by acquiring the image of the object to be filtered. Accordingly, since the color to be deleted is recognized by continuously acquiring the image of the object to be filtered, the user may capture the object including the color to be deleted so that the reference color is set.

As described above, the object to be filtered may include the user's skin, hands, gloves, or soft tissue, saliva, foreign substance, and the like in the patient's oral cavity. The object to be filtered may have color information different from the valid data, and is distinguished from the inside of the patient's oral cavity to be scanned having the valid data.

Specifically describing the reference color range defining operation (S32), the method may again include a reference image acquiring operation (S32*a*) and a reference color range learning operation (S32*b*). In the reference image acquiring operation (S32*a*), at least one image of the object to be filtered including the color to be deleted may be repeatedly acquired. In other words, at least one two-dimensional image data of the object to be filtered may be acquired. At this time, the 'at least one' also includes acquiring the two-dimensional image data, but it is preferable that at least two two-dimensional image data are acquired by performing the capturing so that the reference color range is defined in order to define an effective and accurate reference color range.

The reference image acquiring operation (S32*a*) may be performed separately from the image acquiring operation (S1), and the reference image acquiring operation (S32*a*) may be performed to acquire only the two-dimensional image of the object to be filtered in an environment in which the valid data is not included. For example, in the reference image acquiring operation (S32*a*), a glove worn by the user may be scanned by using a scanner, and two-dimensional image data representing the glove may be acquired. At this time, the object to be filtered may be spaced apart from the scan target having the valid data and scanned.

After acquiring the two-dimensional image data of the object to be filtered from the reference image acquiring operation (S32*a*), in the reference color range learning operation (S32*b*), the reference color or the reference color range may be determined from the image of the object to be filtered. At this time, various methods may be used in determining the reference color or the reference color range. For example, in the image filtering method according to the present disclosure, the reference color range may be determined by using a data density. In the image data acquired in the above-described reference image acquiring operation (S32*a*), a data density appears high for color information that is continuously acquired. When the data density appears high, this is a state in which the two-dimensional image data may be acquired by continuously capturing the object to be filtered, so that the color obtained at more frequencies may be determined and learned as the reference color or reference color range that is the color to be deleted. By learning the reference color range according to the data density as described above, there are advantages in that it is possible to automatically learn the characteristics of the noise data (the color to be deleted appearing in the noise data) and exclude the color to be deleted before the three-dimensional calculating operation (S6), thereby reducing the amount of calculation, increasing the calculation speed, and obtaining the reliable oral cavity model data.

Meanwhile, learning the reference color or the reference color range in the reference color range learning operation (S32*b*) may use an artificial intelligence learning method, and for example, a deep learning method may be used. However, this is illustrative, and any method capable of automatically determining the reference color or the reference color range from at least one two-dimensional image data acquired by scanning the object to be filtered may also be used to implement the image filtering method according to the present disclosure.

Meanwhile, it is determined whether the color information of at least some data acquired in the color acquiring operation (S2) corresponds to the reference color range defined through learning (a reference color determining operation (S4)), and when the color information of the data is included in the reference color range, it is determined that the corresponding data has the color to be deleted to be deleted (filtered) in the two-dimensional image data (S5). Thereafter, by converting the completely filtered two-dimensional image data into the three-dimensional volume data (three-dimensional operating operation (S6)), the user may acquire the entire oral cavity model data of the patient. To acquire the entire oral cavity model data, in the three-dimensional calculating operation (S6), the three-dimensional volume data conversion is performed in a state in which the noise data has been already removed, so that there is an advantage in that it is possible to reduce the amount of calculation, increase the calculation speed, and obtain the reliable oral cavity model data.

Meanwhile, in the image filtering method, the two-dimensional image may be acquired through the scanner, and the three-dimensional volume data may be generated based on the two-dimensional image. The generated three-dimensional volume data may be displayed on a display device or the like in real time. Meanwhile, when the three-dimensional volume data is displayed in real time, a part corresponding to a specific color of the two-dimensional image data may be filtered (deleted) and displayed in real time (filtering operation (S5)). At this time, the 'specific color' of the image data may be a color configuring saliva, the user's glove, and the like that are classified as the noise data when the user of the scanner acquires the entire oral model data of the patient (this is named as the color to be deleted in the specification). The color to be deleted may be learned as the reference color, and a reference color setting operation of defining the color to be deleted may be performed before the three-dimensional calculation operation (S6). When the color to be deleted is set when a three-dimensional virtual model is displayed in the reference color setting operation, thereafter, the reference color determining operation (S4) of determining whether the color to be deleted exists in the two-dimensional image data is performed, and in the filtering operation (S5), when the three-dimensional virtual model is displayed, data containing color information of a part of the two-dimensional image corresponding to the color to be deleted data is deleted to prevent the corresponding color from being displayed. Accordingly, there is an advantage in that the user may acquire reliable data containing necessary color information (i.e., having only valid data such as gums and teeth).

Hereinafter, an image filtering apparatus in which the image filtering method according to the present disclosure is performed will be described.

Figure 7:
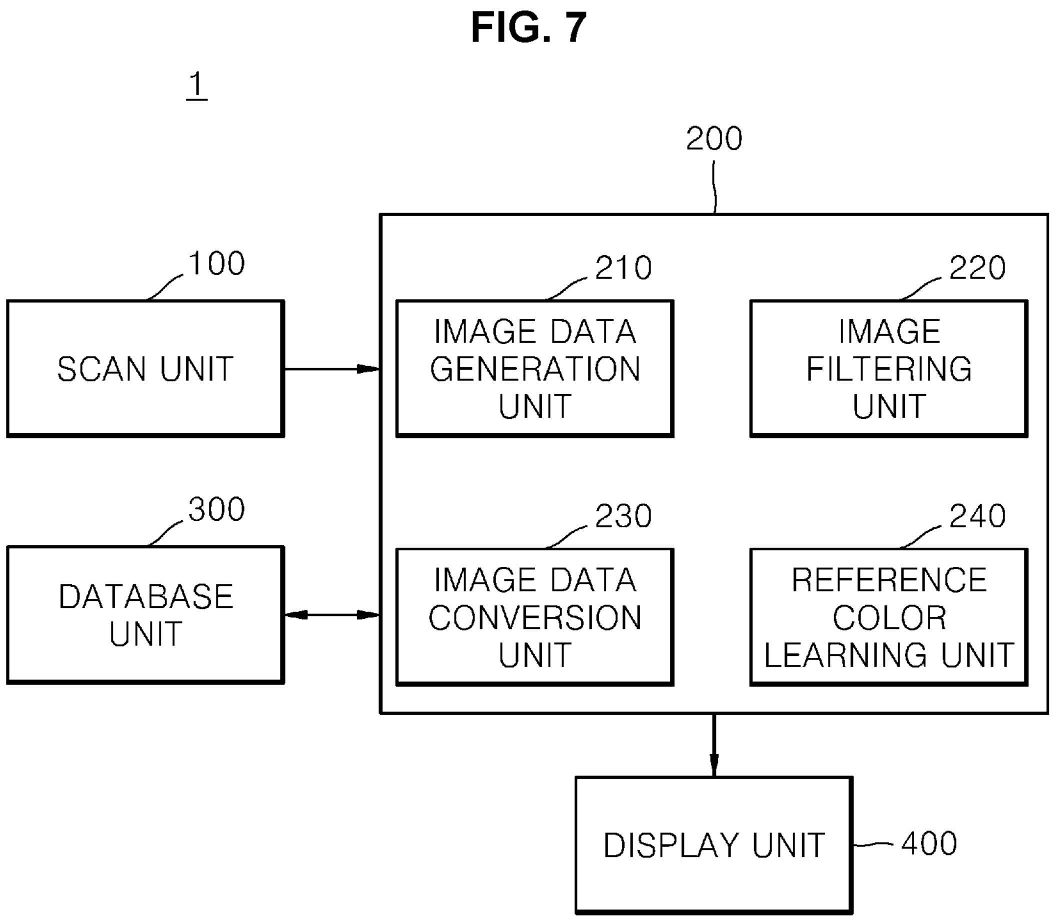
FIG. 7 is a block view of an image filtering device in which the image filter method according to the present disclosure is performed.

FIG. 7 is a block view of the imaging filtering apparatus 1 in which the image filtering method according to the present disclosure is performed. Referring to FIG. 7, the image filtering apparatus 1 according to the present disclosure includes a scan unit 100, a control unit 200, a database unit 300, and a display unit 400.

Hereinafter, each component will be described.

The scan unit 100 may scan a scan target. For example, the scan unit 100 may receive light reflected from the surface of the scan target. Light reflected from the surface of the scan target may be received into an inner portion of the scan unit 100 through an opening formed at one end of the scan unit 100, and light is converted into two-dimensional image data by the control unit 200 to be described below. Meanwhile, light received by the scan process of the scan unit 100 may be, for example, light having a wavelength in a visible ray region. In addition, for example, the scan unit 100 may be a three-dimensional intraoral scanner configured to scan the inside of the patient's oral cavity or the like corresponding to valid data.

Meanwhile, the scan unit 100 may scan not only the scan target but also an object to be filtered having a color to be deleted. As described above, the object to be filtered may be an object having noise data different from the valid data. The object to be filtered is the same as described above.

The control unit 200 may include an image data generation unit 210 configured to generate two-dimensional image data based on light received by the scan unit 100. The image data generation unit 210 may generate light received by the scan unit 100 as two-dimensional image data of a predetermined size, the two-dimensional image data may have a plurality of pixels, and each pixel may have color information. The generated two-dimensional image data may be stored in the database unit 300, and the database unit 300 may also store color information of each pixel.

In addition, the control unit 200 may include an image filtering unit 220. The image filtering unit 220 may filter the color to be deleted of the object to be filtered from the two-dimensional image data acquired from the image data generation unit 210. A reference color corresponding to the color to be deleted may also be designated by a user's selection, or may also be automatically acquired by separately scanning the object to be filtered. The image filtering unit 220 filters pixel data having the color information corresponding to the color to be deleted so that the corresponding part is not converted into three-dimensional volume data.

Meanwhile, the control unit 200 may include an image data conversion unit 230. The image data conversion unit 230 may convert at least a part of the two-dimensional image data generated by the image data generation unit 210 into the three-dimensional volume data. At this time, the three-dimensional volume data is obtained by converting the two-dimensional image data previously filtered by the image filtering unit 220. Accordingly, the converted three-dimensional volume data may include only valid data except for the noise data, and acquire the oral cavity model data of the patient with high reliability.

The control unit 200 may further include a reference color learning unit 240. The reference color learning unit 240 may determine the reference color corresponding to the color to be deleted from at least one two-dimensional image data of the object to be filtered. At this time, the reference color may also be one single color or a color group (color range) within a predetermined range. The learned reference color may be stored in the database unit 300. The reference color stored in the database unit 300 may be reused in another scan process.

The database unit 300 may store the two-dimensional image data generated by the image data generation unit 210, the color information of pixels, the three-dimensional volume data generated by the image data conversion unit 230, the reference color designated by the reference color learning unit 240, and the like. At least a part of the contents stored in the database unit 300 may be used for the operation of the control unit 200 or displayed through the display unit 400. The database unit 300 may also be an object such as a hard disk drive or a flash drive, or may also be a virtual storage system such as a cloud service.

Meanwhile, at least some of the processes performed by the control unit 200 and at least some of the contents stored in the database unit 300 may be visually displayed through the display unit 400. Through the display unit 400, the user may easily confirm whether the image filtering method according to the present disclosure is normally performed. The display unit 400 may be a visual display device such as a monitor or a tablet.

The above description is merely illustrative of the technical spirit of the present disclosure, and various modifications and changes will be possible by those skilled in the art to which the present disclosure pertains without departing from the essential characteristics of the present disclosure.

Accordingly, the embodiments disclosed in the present disclosure are not intended to limit the technical spirit of the present disclosure, but to explain, and the scope of the technical spirit of the present disclosure is not limited by these embodiments. The scope of the present disclosure should be construed by the following claims, and all technical spirits within the scope equivalent thereto should be construed as being included in the scope of the present disclosure.

INDUSTRIAL APPLICABILITY

The present disclosure provides an image filtering method of excluding the part of the image data having the color information corresponding to the preset or learned reference color or reference color range in the three-dimensional volume data conversion even when the valid data and the noise data are scanned together and acquired as the two-dimensional image data.

The invention claimed is:

1. An image filtering method comprising:

an image acquiring operation of acquiring a two-dimensional image of a scan target having a valid data part including a tooth inside an oral cavity through a scanner;

a color acquiring operation of acquiring color information from at least some data of the two-dimensional image acquired from the image acquiring operation;

a filtering operation of determining the at least some data as data to be deleted having a color to be deleted and deleting the at least some data within the two-dimensional image data when the color information of the at least some data is included within a reference color range that is a color range of an object to be filtered distinguished from an inside of the oral cavity in the color acquiring operation; and a three-dimensional calculating operation of converting two-dimensional data having only the valid data part by deleting the data to be deleted through the filtering operation into three-dimensional volume data.

2. The image filtering method of claim 1, further comprising: a reference color determining operation of determining whether the color information of the at least some data acquired in the color acquiring operation is included within the reference color range, wherein the filtering operation determines the at least some data determined as the reference color range from the reference color determining operation as the data to be deleted to delete the at least some data within the two-dimensional image data.

3. The image filtering method of claim 2, further comprising: a reference color setting operation of setting the color to be deleted, wherein the color to be deleted in the reference color setting operation is designated through a user interface.

4. The image filtering method of claim 3, wherein the size of the reference color range is adjustable through the user interface with respect to the color to be deleted.

5. The image filtering method of claim 1, wherein the color information is information expressed by using an RGB additive color mixture method.

6. An image filtering method comprising:

an image acquiring operation of acquiring a two-dimensional image of a scan target having a valid data part including a tooth inside an oral cavity and a noise data part including an object to be filtered through a scanner;

a modeling operation of generating a three-dimensional virtual model based on filtered two-dimensional image;

a displaying operation of visually displaying the three-dimensional virtual model; and a filtering operation of filtering the noise data part corresponding to the color to be deleted that is a color of the object to be filtered distinguished from the inside of the oral cavity in the two-dimensional image to generate the filtered two-dimensional image, before being converted into three-dimensional volume data, before the modeling operation, wherein the modeling operation generates the three-dimensional virtual model with the filtered two-dimensional image data having only the valid data part by deleting the data having the color to be deleted, wherein a user directly designates the color to be deleted on the two-dimensional image data in the filtering operation.

7. The image filtering method of claim 6, wherein the filtering operation further includes: a reference color setting operation of setting the color to be deleted from the object to be filtered; and a reference color determining operation of determining whether the color to be deleted exists in the two-dimensional image.

8. The image filtering method of claim 7, wherein the reference color setting operation is set by the user's selection, or set based on the image of the object to be filtered.

9. An image filtering method comprising:

an image acquiring operation of acquiring a two-dimensional image of a scan target having a valid data part including a tooth inside an oral cavity and a noise data part including an object to be filtered through a scanner;

a color acquiring operation of acquiring color information from at least one pixel of the two-dimensional image acquired from the image acquiring operation;

a reference color range defining operation of defining a color range of the object to be filtered as a reference color range based on an image of the object to be filtered distinguished from the inside of the oral cavity;

a reference color determining operation of determining whether color information of the at least one pixel acquired in the color acquiring operation is included within the reference color range defined;

a filtering operation of determining the at least one pixel as pixel to be deleted having a color to be deleted and deleting the at least one pixel which corresponds to the noise data within the two-dimensional image data before being converted into three-dimensional volume data when the color information of the at least one pixel is included within the reference color range in the color determining operation; and a three-dimensional calculating operation of converting filtered two-dimensional data having only the valid data part by deleting the pixel to be deleted through the filtering operation into three-dimensional volume data, wherein in the reference color range defining operation, the image representing the object to be filtered including at least one pixel having the color to be deleted is acquired repeatedly, and the reference color range is defined by using a data density.

10. The image filtering method of claim 9, wherein the reference color range defining operation includes:

a reference color acquiring operation of repeatedly acquiring at least one image of the object to be filtered including the color to be deleted; and a reference color range learning operation of determining the reference color range from the image of the object to be filtered acquired from the reference image acquiring operation.

11. The image filtering method of claim 10, wherein the reference color range learning operation learns an overlapping color from at least one image acquired through the reference image acquiring operation as the reference color range.

12. The image filtering method of claim 9, wherein the color information is information expressed by using an RGB additive color mixture method.

* * * * *